US012676218B2

(12) United States Patent
Pinter et al.

(10) Patent No.: US 12,676,218 B2
(45) Date of Patent: *Jul. 7, 2026

(54) AUTOMATED TRANSCRIPTION AND DOCUMENTATION OF TELE-HEALTH ENCOUNTERS

(71) Applicant: TELADOC HEALTH, INC., Purchase, NY (US)

(72) Inventors: Marco Pinter, Santa Barbara, CA (US); Charles S. Jordan, Santa Barbara, CA (US); Yulun Wang, Goleta, CA (US); Ole Eichhorn, Westlake Village, CA (US)

(73) Assignee: TELADOC HEALTH, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/401,662

(22) Filed: Jan. 1, 2024

(65) Prior Publication Data

US 2024/0136033 A1 Apr. 25, 2024

Related U.S. Application Data

(63) Continuation of application No. 15/961,705, filed on Apr. 24, 2018, now Pat. No. 11,862,302.

(60) Provisional application No. 62/536,907, filed on Jul. 25, 2017, provisional application No. 62/489,380, filed on Apr. 24, 2017.

(51) Int. Cl.
| | |
|---|---|
| *G16H 10/60* | (2018.01) |
| *G06N 3/084* | (2023.01) |
| *G06N 20/00* | (2019.01) |
| *G16H 80/00* | (2018.01) |

(52) U.S. Cl.
CPC ............. *G16H 10/60* (2018.01); *G06N 3/084* (2013.01); *G06N 20/00* (2019.01); *G16H 80/00* (2018.01)

(58) Field of Classification Search
CPC .............................. G16H 15/00; G16H 80/00
See application file for complete search history.

(56) References Cited

U.S. PATENT DOCUMENTS

| | | | |
|---|---|---|---|
| 11,862,302 B2 * | 1/2024 | Pinter ................... | G06N 3/044 |
| 2012/0323572 A1 * | 12/2012 | Koll ....................... | G16Z 99/00 |
| | | | 704/235 |

(Continued)

FOREIGN PATENT DOCUMENTS

WO     WO-2014197669 A1 * 12/2014     ........... G06F 40/143

OTHER PUBLICATIONS

Lee, Chien-Nan, et al. "Usage of smart mobile device at the telemedicine." 2011 International Conference on Machine Learning and Cybernetics. vol. 2. IEEE, 2011. (Year: 2011).*

*Primary Examiner* — Jason B Dunham
*Assistant Examiner* — Constantine Siozopoulos

(57) ABSTRACT

Automatically generating a structured medical note during a remote medical consultation using machine learning. A provider tele-presence device may receive audio from a medical provider. A medical documentation server may be coupled to the network. A machine learning network receives audio data from the provider tele-presence device, the machine learning network generating a structured medical note based on the received audio data, and wherein the structured medical note is stored in the medical documentation server in association with an identity of a patient.

30 Claims, 5 Drawing Sheets

(56)             References Cited

U.S. PATENT DOCUMENTS

2017/0116384 A1 *   4/2017   Ghani  ................... G16H 70/20
2018/0150605 A1 *   5/2018   Co  ........................ G16H 40/20

* cited by examiner

FIG. 3

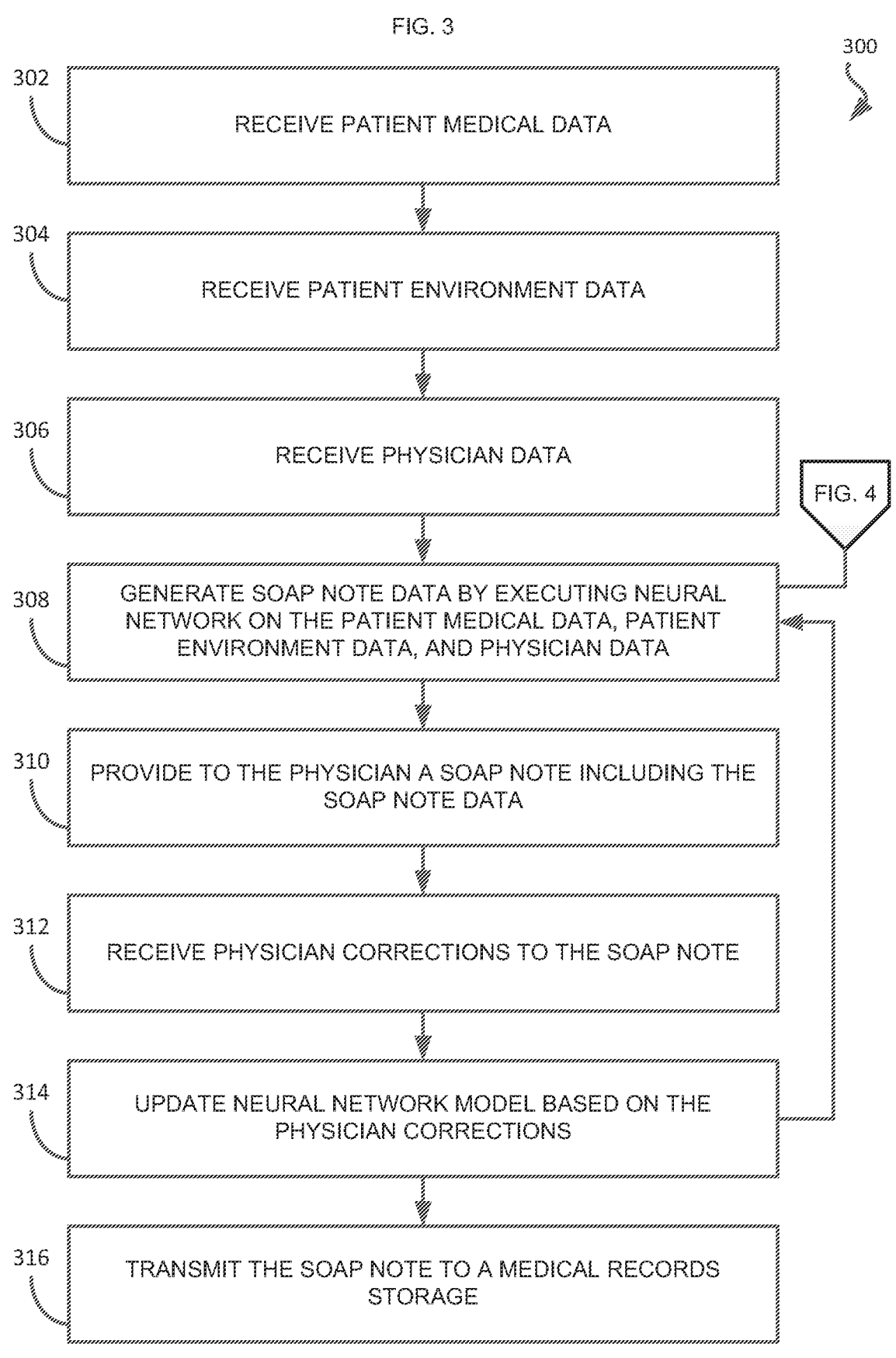

300

302  RECEIVE PATIENT MEDICAL DATA

304  RECEIVE PATIENT ENVIRONMENT DATA

306  RECEIVE PHYSICIAN DATA

FIG. 4

308  GENERATE SOAP NOTE DATA BY EXECUTING NEURAL NETWORK ON THE PATIENT MEDICAL DATA, PATIENT ENVIRONMENT DATA, AND PHYSICIAN DATA

310  PROVIDE TO THE PHYSICIAN A SOAP NOTE INCLUDING THE SOAP NOTE DATA

312  RECEIVE PHYSICIAN CORRECTIONS TO THE SOAP NOTE

314  UPDATE NEURAL NETWORK MODEL BASED ON THE PHYSICIAN CORRECTIONS

316  TRANSMIT THE SOAP NOTE TO A MEDICAL RECORDS STORAGE

400

402

IDENTIFY SPOKEN CONTENT UTTERED BY THE PHYSICIAN

404

IDENTIFY A PORTION OF THE SPOKEN CONTENT FOR INSERTION INTO A SOAP NOTE

406

CONVERT THE IDENTIFIED PORTION OF THE SPOKEN CONTENT INTO SOAP NOTE DATA

AUTOMATED TRANSCRIPTION AND DOCUMENTATION OF TELE-HEALTH ENCOUNTERS

CROSS-REFERENCE TO RELATED APPLICATIONS

This application claims priority to U.S. provisional application No. 62/489,380, filed Apr. 24, 2017, which is hereby incorporated by reference in its entirety.

TECHNICAL FIELD

The present technology pertains to tele-health systems, and more specifically to the automated production of medical documentation.

BACKGROUND

Studies have shown that as little as one-third of physician time is spent visiting with patients, and much of the remaining two-thirds of physician time is dedicated to documenting those patient encounters. These are often documented in the form of a SOAP (e.g., "Subjective, Objective, Assessment, and Plan") note. A SOAP note may be entered into a medical record for the patient, typically an electronic medical record ("EMR"), and documents a patient statement of a reason for visiting a physician and the patient history of illness, observations of the patient made by the physician and other healthcare professionals (e.g., vital signs, weight, examination findings, and the like), medical diagnoses of the patient symptoms, and a determined treatment plan for the patient.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only example embodiments of the disclosure and are not therefore to be considered to be limiting of its scope, the principles herein are described and explained with additional specificity and detail through the use of the accompanying drawings in which.

DETAILED DESCRIPTION

Figure 1:
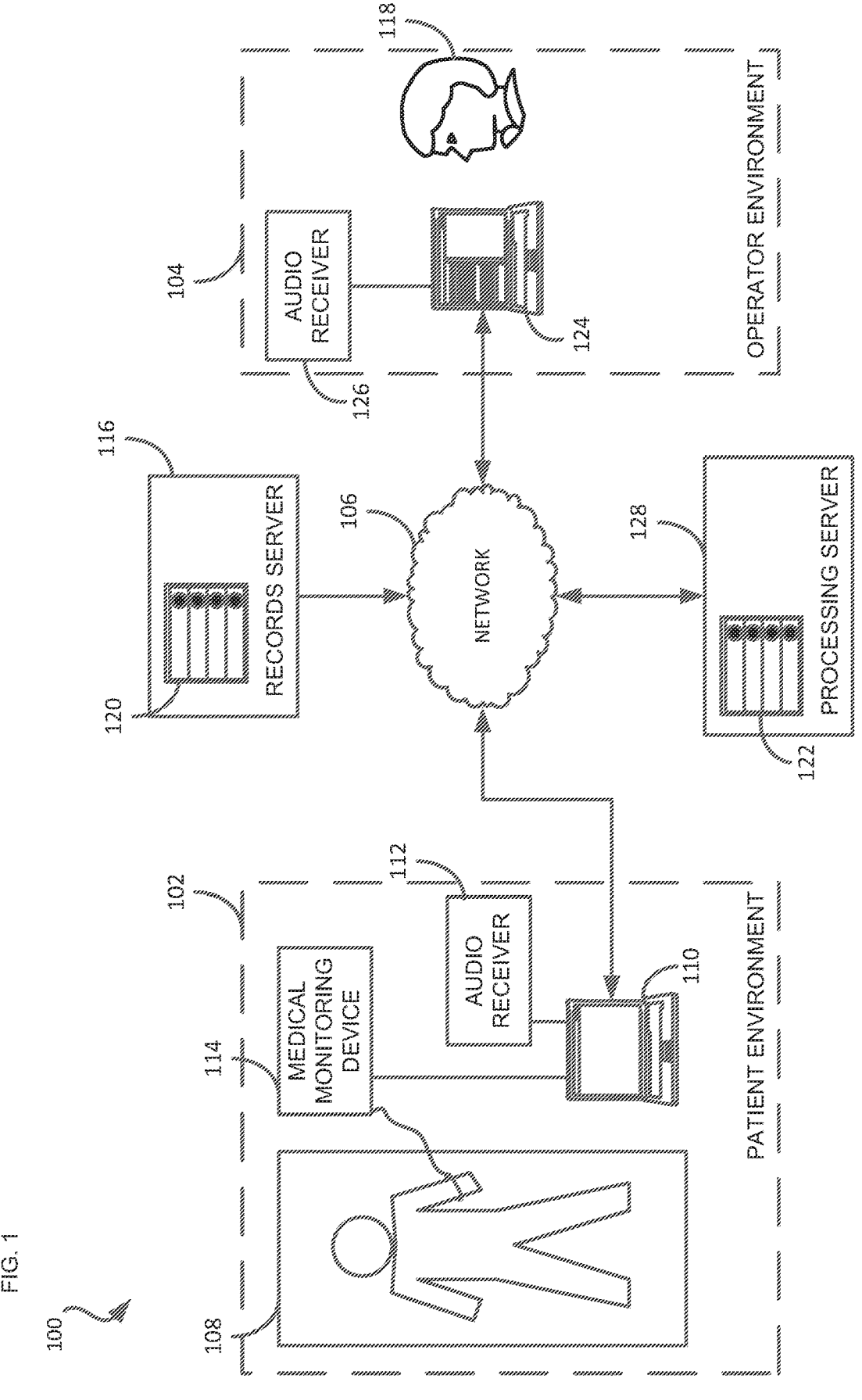
FIG. 1 illustrates a tele-health system, according to one embodiment of the present disclosure.

Various embodiments of the disclosure are discussed in detail below. While specific implementations are discussed, it should be understood that this is done for illustration purposes only. A person skilled in the relevant art will recognize that other components and configurations may be used without departing from the spirit and scope of the disclosure.

It should be understood at the outset that although illustrative implementations of one or more embodiments are illustrated below, the disclosed apparatus and methods may be implemented using any number of techniques. The disclosure should in no way be limited to the illustrative implementations, drawings, and techniques illustrated herein, but may be modified within the scope of the appended claims along with their full scope of equivalents.

The automated generation of a SOAP note from a live encounter can greatly increase the time a physician has available to be with patients. Medical providers, such as physicians for example, typically devote a significant portion of the day to administrative tasks such as generating documentation of patient consultations and the like. In particular, the manual production of SOAP notes is a time consuming and tedious process which often takes up a sizable portion of the workday.

The disclosed technology may provide additional benefits in the context of tele-health encounters. A typical tele-health encounter may involve a patient and one or more remotely located physicians or healthcare providers—devices located in the vicinity of the patient and the providers allow the patients and providers to communicate with each other using, for example, two-way audio and/or video conferencing.

A tele-presence device may take the form of a desktop, laptop, tablet, smart phone, or any computing device equipped with hardware and software configured to capture, reproduce, transmit, and receive audio and/or video to or from another tele-presence device across a communication network. Tele-presence devices may also take the form of tele-presence robots, carts, and/or other devices such as those marketed by InTouch Technologies, Inc. of Goleta, California, under the names INTOUCH VITA, INTOUCH LITE, INTOUCH VANTAGE, INTOUCH VICI, INTOUCH VIEWPOINT, INTOUCH XPRESS, and INTOUCH XPRESS CART. The physician tele-presence device and the patient tele-presence device may mediate an encounter, thus providing high-quality audio capture on both the provider-side and the patient-side of the interaction.

Furthermore, unlike an in-person encounter where a smart phone may be placed on the table and an application started, a tele-health-based auto-scribe can intelligently tie into a much larger context around the live encounter. The tele-health system may include a server or cloud infrastructure that provides the remote provider with clinical documentation tools and/or access to the electronic medical record ("EMR") and medical imaging systems (e.g., such as a "picture archiving and communication system," or "PACS," and the like) within any number of hospitals, hospital networks, other care facilities, or any other type of medical information system. In this environment, the software may have access to the name or identification of the patient being examined as well as access to their EMR. The software may also have access to, for example, notes from a nursing staff that may have just been entered. Increased input to the system may make system outputs more robust and complete. The outputs can be automatically incorporated into the appropriate electronic medical record (EMR).

There may also be other advantages and features, such as, without limitation:

Prior to a remote physician initiating a tele-health encounter or session, the patient-side tele-presence device may proactively prompt the patient with questions and the patient responses may be added to the note.

Utilize context of the physician interaction with a clinical documentation tool to add to completeness and robustness of a SOAP note generated by the physician or automatically by the system.

Utilize context of other physician user interface ("UI") interactions. For instance, and without imputing limitation, the system can track whether the provider activated a camera zoom function to more closely examine the patient's eyes, a wound, and the like. The system can also track whether the provider activated a camera pan and/or tilt function to look at a chart or vitals monitor. Moreover, the system can track whether the provider accessed output from a medical peripheral device in the vicinity of the patient, such as a stethoscope, otoscope, sonogram, ultrasound, dermal camera, and the like.

The system can apply computer vision techniques to the video to perform scene recognition for the creation of additional context and content for SOAP note generation. This can include, for example and without imputing limitation, understanding what part of a patient is being looked at and automatically analyzing vital signs monitors.

The system may make use of a human or artificial intelligence ("AI") language translator that has access to session audio and/or video. For example, the language translator can mediate by translating the physician audio from English into a native language of the patient and translate the patient responses back into English for both the physician and an AI scribe.

In one example, a physician uses a clinical documentation tool within a tele-health software application on a laptop to review a patient record. The physician can click a "connect" button in the tele-health software that connects the physician tele-presence device to a tele-presence device in the vicinity of the patient. In one example, the patient-side tele-presence device may be a mobile tele-presence robot with autonomous navigation capability located in a hospital, such as an INTOUCH VITA. The patient-side tele-presence may automatically navigate to the patient bedside, and the tele-health software can launch a live audio and/or video conferencing session between the physician laptop and the patient-side tele-presence device such as disclosed in U.S. Pub. No. 2005/02044381 and hereby incorporated by reference in its entirety.

In addition to the live video, the tele-health software can display a transcription box. Everything the physician or patient says can appear in the transcription box and may be converted to text. In some examples, the text may be presented as a scrolling marquee or an otherwise streaming text.

Transcription may begin immediately upon commencement of the session. The physician interface may display a clinical documentation tool, including a stroke workflow (e.g., with a NIHSS, or National Institutes of Health Stroke Scale, score, a tPA, or tissue plasminogen activator, calculator, and the like) such as disclosed in U.S. Pub. No. 2009/0259339 and hereby incorporated by reference in its entirety. Furthermore, the stroke workflow may be provided in the physician interface alongside a live SOAP note window.

The system can also monitor and process "sidebar" conversations. Such conversations can include discussions taking place between the physician and personnel at the patient site via, for example, a handset on the patient-side tele-presence device. Additionally, in a case in which there are multiple remote parties participating in the session via a multipoint conference, conversations between the remote participants can also be monitored and processed.

The system may distinguish among participants using voice recognition techniques. In one embodiment, the system may only populate the SOAP note with content from a specified participant such as, for example and without imputing limitation, the physician. In some examples, the audio can be processed by multiple neural networks or preprocessed by various services. For example, the audio may be first fed through a trained speech-to-text network such as Amazon® Transcribe® or Nuance® Dragon® and the like. The transcribed output text may then be used as input into a SOAP note generated by the physician. A network can be trained on a portion (e.g., 80%) of SOAP notes created in such a way and then tested against a remaining portion (e.g., 20%) of the SOAP notes.

As an encounter progresses, the system can automatically fill in the SOAP note. A deep learning neural network or other trained machine learning model analyzing the encounter can run concurrent to the encounter and update itself using automatic and/or physician-provided feedback. In some examples, early entries in the SOAP note may be inaccurate, but later entries will become increasingly correct as greater context becomes available throughout the encounter. While discussed in the context of a neural network, it is understood that various and multiple machine learning networks and methodologies can be used to train a model for use in automatically generating a SOAP note. For example, and without imputing limitation, logit, sequential logit, Hidden Markov Model, and other machine learning networks and models may be used as will be apparent to a person having ordinary skill in the art.

Further, the system may diarize audio and process speaker identity as further context and input for the deep learning neural network. In some examples, dedicated microphones on both the patient-side and physician-side of the system can inform the system which speaker is associated with what audio content through, for example, dedicated and predefined audio channels. In such a case, an audio channel associated with the physician-side of the system may be processed separately than, for example, an audio channel associated with the patient-side. Further diarization techniques can be applied to both audio channels to further distinguish, for example, a patient statement from that of an on-site attendant (e.g., nurse and the like) statement.

The SOAP note may be multimedia in that it includes text, pictures, clips or any other media relevant to the encounter. For example, a SOAP note may include an audio recording of either or both of the physician or patient. In some examples, the SOAP note can be linked to a PACS or similar in order to both directly and indirectly include imaging data and the like.

In one example, the physician may choose to add or change certain things in a live SOAP note as it is generated. The physician input can be integrated as another data source in the neural network. In some examples, the physician input can be used to update the neural network while the SOAP note is generated and thus increase the quality of the generated SOAP note as the encounter progresses.

In another example, the system may include meta-information derived from a patient speech in addition to performing patient speech transcription. For example and without imputing limitation, the system may track and make note of inflection, slurring, and pauses between a physician question and the start of the patient answer. This and other types of meta-information may be valuable to the SOAP note context.

The system may also track physician interactions to add further context for SOAP note generation. Physician interactions can include interactions with a clinical documentation tool (e.g., a NIHSS stage being viewed by the physician) and interactions with an endpoint UI (e.g., zooms, pans, tilts, switches between cameras, switches to a stethoscope, and the like). In some examples, the physician may toggle what input is tracked by, for example, holding space bar to pause tracking (e.g., where the physician is reacting to a matter unrelated to the patient interaction and the like).

The system may recognize references to content in the image and automatically capture the image and insert it in the documentation. For example, if the physician instructed the patient to "hold your hands up in front of you", then the system may automatically capture an image or video clip of the subsequent activity. The system may also perform other visual recognition on video or images from the patient-side camera to further add context and make the note more complete and robust.

The system may also utilize other cloud-based AI systems to bring greater context to a given clinical situation. For example, if a CT scan is uploaded to a cloud service for analysis, the resulting analysis may be included in the SOAP note. In some examples, the system may directly interface with a PACS and the like to retrieve imaging data.

Upon completion of the live encounter with the patient, the physician can end the audio and/or video session. The video window closes and, in the case of a robotic patient-side endpoint, the patient-side tele-presence device may navigate back to its dock. The physician-side interface may display a patient record (e.g., within a clinical documentation tool). In some examples, the generated SOAP note may be displayed next to the patient record. The SOAP note may be editable so the physician can make changes to the SOAP note. When satisfied, the physician may sign the note and click a "Send" button to automatically insert the SOAP note into an EMR for that patient. Further, as discussed above, the physician changes to the generated SOAP note can be fed back into the neural network in order to further improve SOAP note generation. In some examples, the neural network can train a physician-specific model based on multiple SOAP note changes received from a particular physician.

The neural network can be one or more trained Deep Learning networks. The architecture of the neural network can be a single network or layers of networks through which data and outputs can be cascaded. The network may have been trained by data over several thousand encounters, using various input data, including, but not limited to, two-way audio recording from an encounter, interface data and/or visual data from the encounter, and meta-data from the encounter (e.g., pause durations, postures, UI interactions, and the like).

The neural network output data may include a SOAP note produced from the encounter. The SOAP note may be cleaned and curated by a third party or the responsible physician. In some examples, the SOAP note can be provided back to the neural network as, for example, further training data in order to improve the accuracy of the neural network for later encounter.

In one embodiment, the neural network can be a Recurrent Neural Network (RNN) built on the CaFE framework from UC Berkeley. The network may be embodied in a software module that executes on one or more servers coupled to the network in the tele-health system. Alternatively, the module may execute on a patient tele-presence device or a physician tele-presence device. The output of the module can include transcribed audio, a SOAP note, and the like. Further, in some examples, the module may transmit the output from a server to multiple and various tele-presence devices, from one tele-presence device to another, and/or to a medical records or documentation server where it can be stored in association with a patient medical record.

FIG. 1. Depicts a system 100 for automatically generating a SOAP note from a tele-encounter between a patient 108 in a patient environment 102 and a physician 118 in an operator environment 104. The physician 118 and patient 108 may be located in different locations and communicate with each other over a network 106 which may include one or more Internet linkages, Local Area Networks ("LAN"), mobile networks, and the like.

The patient 108 and the physician 118 can interact via a patient endpoint 110 in the patient environment 102 and a physician endpoint 124 in the operator environment 104. While depicted in FIG. 1 as computer terminals, it will be understood by a person having ordinary skill in the art that either or both of the endpoint 110 and the endpoint 124 can be a desktop computer, a mobile phone, a remotely operated robot, a laptop computer, and the like. In some examples, the endpoint 110 can be a remotely operated robot which is controlled by the physician 118 through the endpoint 124 which is a laptop computer.

Nevertheless, the endpoint 112 may include a patient-side audio receiver 112 and the endpoint 124 can include a physician-side audio receiver 126. The patient-side audio receiver 112 and the physician-side audio receiver 126 can provide audio data to a processing server 128 via respective endpoint 110 and endpoint 124 over the network 106. In some examples, the audio data is received as particular channels and may assist the processing server 128 in diarizing audio inputs to the system 100. The processing server 128 may be a remotely connected computer server 122. In some examples, the processing server 128 may include a virtual server and the like provided over a cloud-based service, as will be understood by a person having ordinary skill in the art.

The physician 118 may retrieve and review EMR and other medical data related to the patient 108 from a networked records server 116. The records server 116 can be a computer server 120 remotely connected to the physician endpoint 124 via the network 106 or may be onsite with the physician 118 or the patient 108.

In addition to patient audio and EMR, the physician 118 can receive diagnostic or other medical data from the patient 108 via a medical monitoring device 114 hooked up to the patient 108 and connected to the patient endpoint 110. For example, a heart-rate monitor may be providing cardiovascular measurements of the patient 108 to the patient endpoint 110 and on to the physician 118 via the network 106 and the physician endpoint 124. In some examples, multiple medical monitoring devices 114 can be connected to the patient endpoint 110 in order to provide a suite of data to the physician 118. Other devices such as, for example, a camera and the like may be connected to the patient endpoint 110 and/or the physician endpoint 124 (not depicted) and can further provide environmental and other contextual to the system 100. The processing server 128 can intercept or otherwise receive data transmitted between the operator environment 104 and the patient environment 102.

Figure 2:
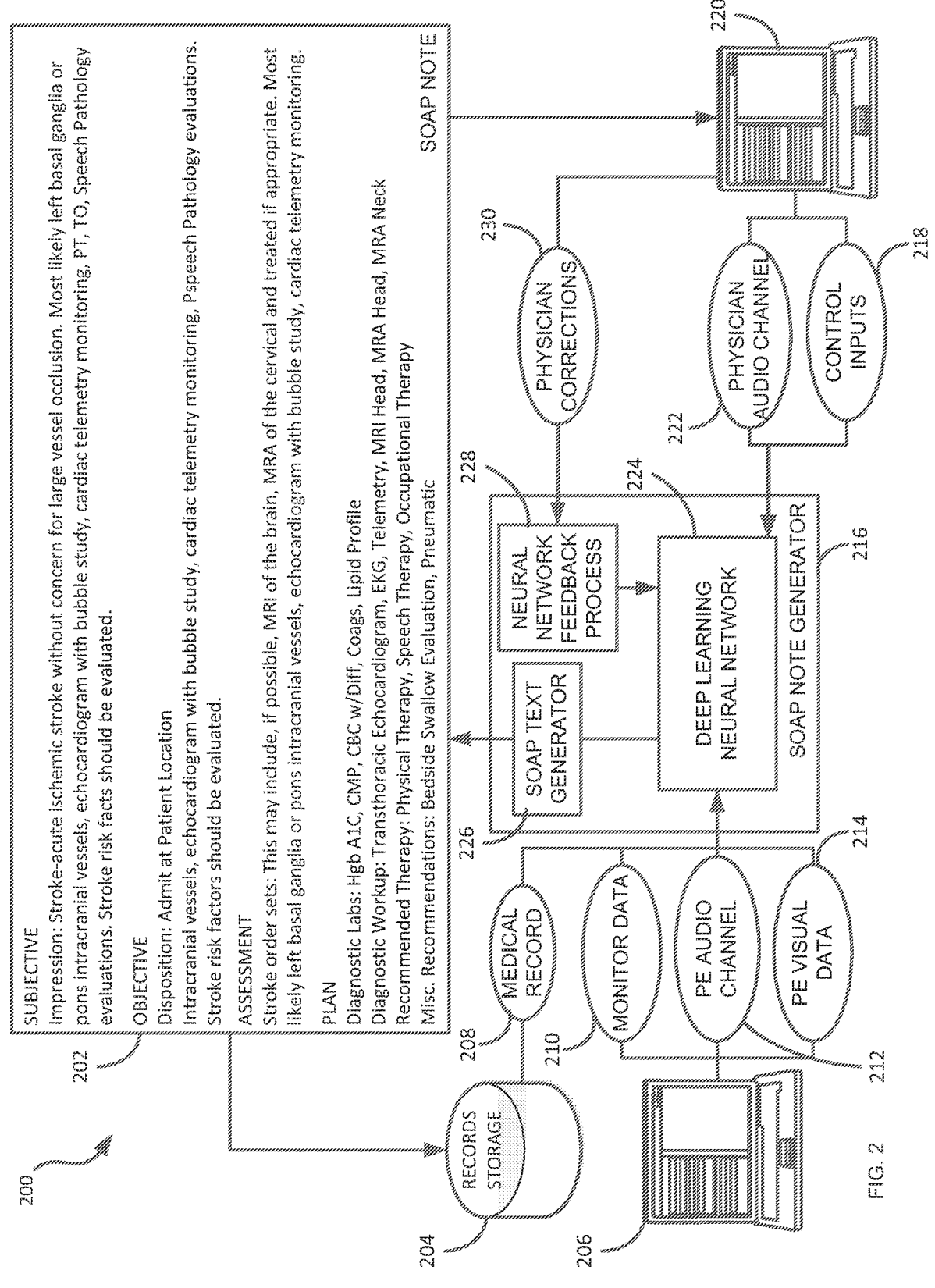
FIG. 2 illustrates a tele-health system, according to one embodiment of the present disclosure.
Figures 3, 4:
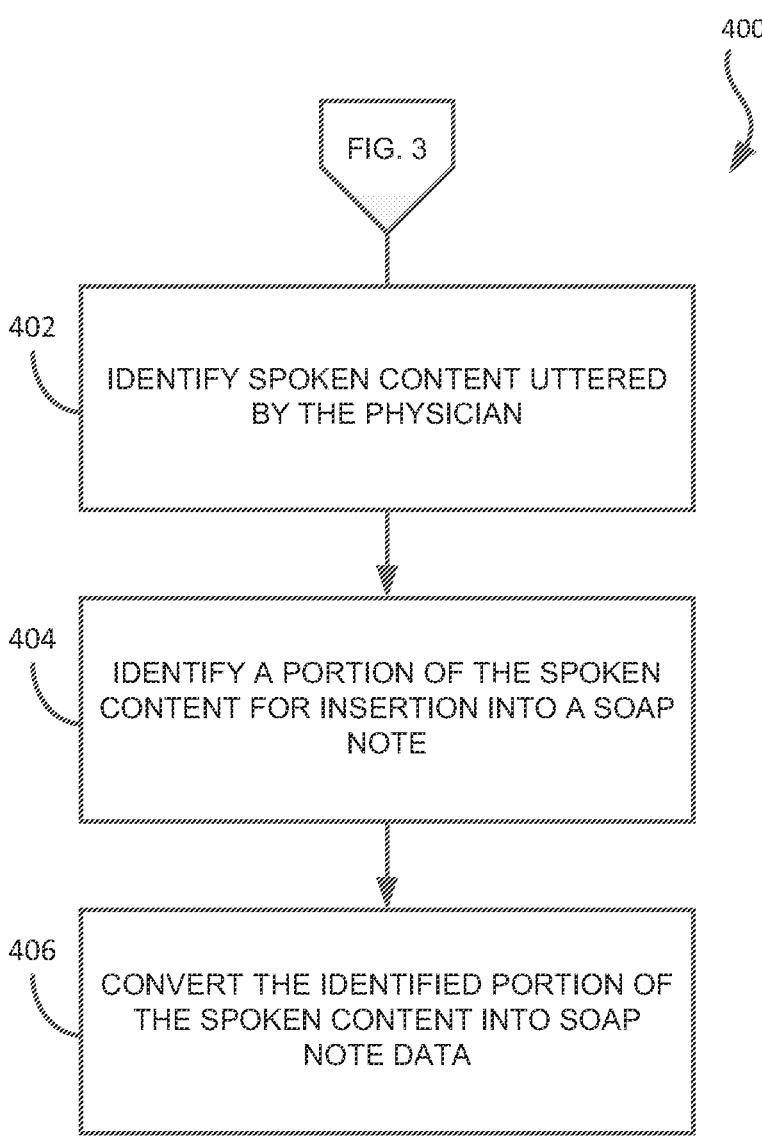
FIG. 3 is a flowchart illustrating a method for generating a SOAP note, according to one embodiment of the present disclosure.
FIG. 4 is a flowchart illustrating a method for converting spoken language into SOAP note data.

FIG. 2 and FIG. 3 depict in greater detail by which a system 200 and a method 300 respectively can automatically produce a SOAP note 202 from an encounter between a patient and a physician. A SOAP note 202 may include, for example, fields for subjective information, objective information, assessments, and treatment plans as will be understood by a person having ordinary skill in the art. In some examples, the SOAP note 202 can include multimedia information such as video or audio (not depicted).

A SOAP note generator 216 may be provided on a processing server 128 or otherwise connected to a patient endpoint 206 and a physician endpoint 220. In some examples, the SOAP note generator 216 can be located directly on the physician endpoint 220 or the patient endpoint 206. The physician endpoint 220 and the patient endpoint 206 may be similar to physician endpoint 124 and the patient endpoint 110 depicted in FIG. 1 and discussed above. In some other examples, the SOAP note generator 216 can be provided as a distributed system and may include components and/or processes run on the processing server 128, the patient endpoint 206, the physician endpoint 220, remotely provided services over, for example, the network 106, or some combination thereof.

The SOAP note generator 216 may include a deep learning neural network 224 for processing input data, a SOAP text generator 226 for converting outputs from the deep learning neural network 224 into text for the SOAP note, and a neural network feedback process 228 for updating the deep learning neural network 224 responsive to, for example, physician feedback. The SOAP note generator 216 can be communicatively connected to the patient endpoint 206 and the physician endpoint 220 and may further be communicatively connected to a records storage 204. The records storage 204 can receive the generated SOAP note 202 for storage in, for example, an EMR associated with a patient. In some examples, the records storage 204 can provide an EMR or other historical data to the SOAP note generator 216.

The SOAP note generator 216 can receive patient medical data as a medical record 208 and monitor data 210 (operation 302). The medical record 208 can be an EMR received from the records storage 204. In some examples the medical record 208 can include other SOAP notes, notes from nurses at the time of the current visit, and other data. The monitor data 210 can include data from any or all of multiple devices such as an EKG, blood pressure monitor, thermometer, and the like as will be apparent to a person having ordinary skill in the art.

The SOAP note generator 216 can also receive patient environment data (operation 304). Patient environment data can include a patient environment audio channel 212 as well as patient environment visual data 214. In some examples, either or both of the patient environment audio channel 212 and the patient environment visual data 214 can be preprocessed by, for example, text-to-speech software provided by a third party.

A physician audio channel 222 and control inputs 218 may be provided to the SOAP note generator 216 (operation 306). In some examples, the physician audio channel 222 can be limited by an attending physician through, for example, turning off recording and the like by pressing and/or depressing a space bar. The control inputs 218 can include, for example, the pressing and depressing the space bar above and other UI interactions on the physician endpoint 220. For example, the attending physician may be able to control a camera in the patient environment and camera control actions performed by the physician such as, for example, camera zoom, sweep, pan, focus, and the like as will be understood by a person having ordinary skill in the art.

The deep learning neural network 224 may generate SOAP note data using the physician data (e.g., the physician audio channel 222 and the control inputs 218) and the patient environment and medical data (e.g., the medical record 208, the monitor data 210, the patient environment audio channel 212, and the patient environment visual data 214) as inputs (operation 308). In some examples, specific physician audio data may be identified and only that data will be used to generate SOAP note data. FIG. 4 depicts one such method 400 for further processing the physician audio channel 222.

Spoken content uttered by the physician may be identified (operation 402). The physician audio channel 222 may include other audio noise such as other voices (e.g., other physicians performing tele-health consultations) or arbitrary environmental sounds the like. The identified content may be segments of spoken content provided by the physician amongst a larger volume of spoken content from the physician otherwise not intended to be included in the SOAP note data. In some examples, this can be performed on the physician endpoint 220 via UI interactions performed by the physician (e.g., pressing a record a key and the like) or through an automated process (e.g., voice command interaction and the like).

The spoken content may be processed to identify a portion for insertion into a SOAP note (operation 404). The identified portion may be provided to the SOAP note generator 216 as input into the deep learning neural network 224 or, in some examples, may be provided to the SOAP text generator 226. Nevertheless, the identified portion of spoken content may be converted into SOAP note data (operation 406). In some examples, the SOAP note data may be able to be directly inserted into the SOAP note 202 (e.g., as string variables and the like). In some other examples, the SOAP note generator 216 may further process the data through a SOAP text generator 226 for insertion into the SOAP note 202.

Returning to FIG. 3, the generated SOAP note 202 may be provided to the physician through the physician endpoint 220 (operation 310). In some examples, the SOAP note 202 may be provided as a final product after completion of the tele-health interaction with the patient. In other examples, the SOAP note 202 can be provided in real time to the physician endpoint 220 as a dynamic and on-the-fly generated UI element.

The physician may make physician corrections 230 to the SOAP note 202 and the corrections may be received by the neural network feedback process 228 of the SOAP note generator 216 (operation 312). In some examples, particularly where the SOAP note 202 is provided to the physician endpoint 220 in real time, the physician corrections 230 can be maintained in the UI while the at the same time being processed by the neural network feedback process 228.

The deep learning neural network 224 may be updated by the neural network feedback process 228 using the physician corrections 230 (operation 312). The neural network feedback process 228 may update the deep learning neural network 224 through, for example, a gradient descent algorithm and back propagation and the like as will be apparent to a person having ordinary skill in the art. In some examples, the deep learning neural network 224 may be updated in real time or near real time. In other examples, the neural network feedback process 228 may perform model updates as a background process on a mirror version of the deep learning neural network 224 and directly update the deep learning neural network 224 once the mirror version has converged on an updated model. In other examples, the neural network feedback process 228 may perform updates on a scheduled or through a batch process. The updates can be performed on a singular device or may be performed across parallelized threads and processes and the like.

Once the SOAP note 202 is reviewed by the physician on, for example, the physician endpoint 220, the SOAP note 202 can be transmitted to the records storage 204 (operation 316). The SOAP note 202 may be added to the medical record 208 of a patient, for example, to be used later as input to the SOAP note generator 216 during a future tele-health conference with the same patient.

Figure 5:
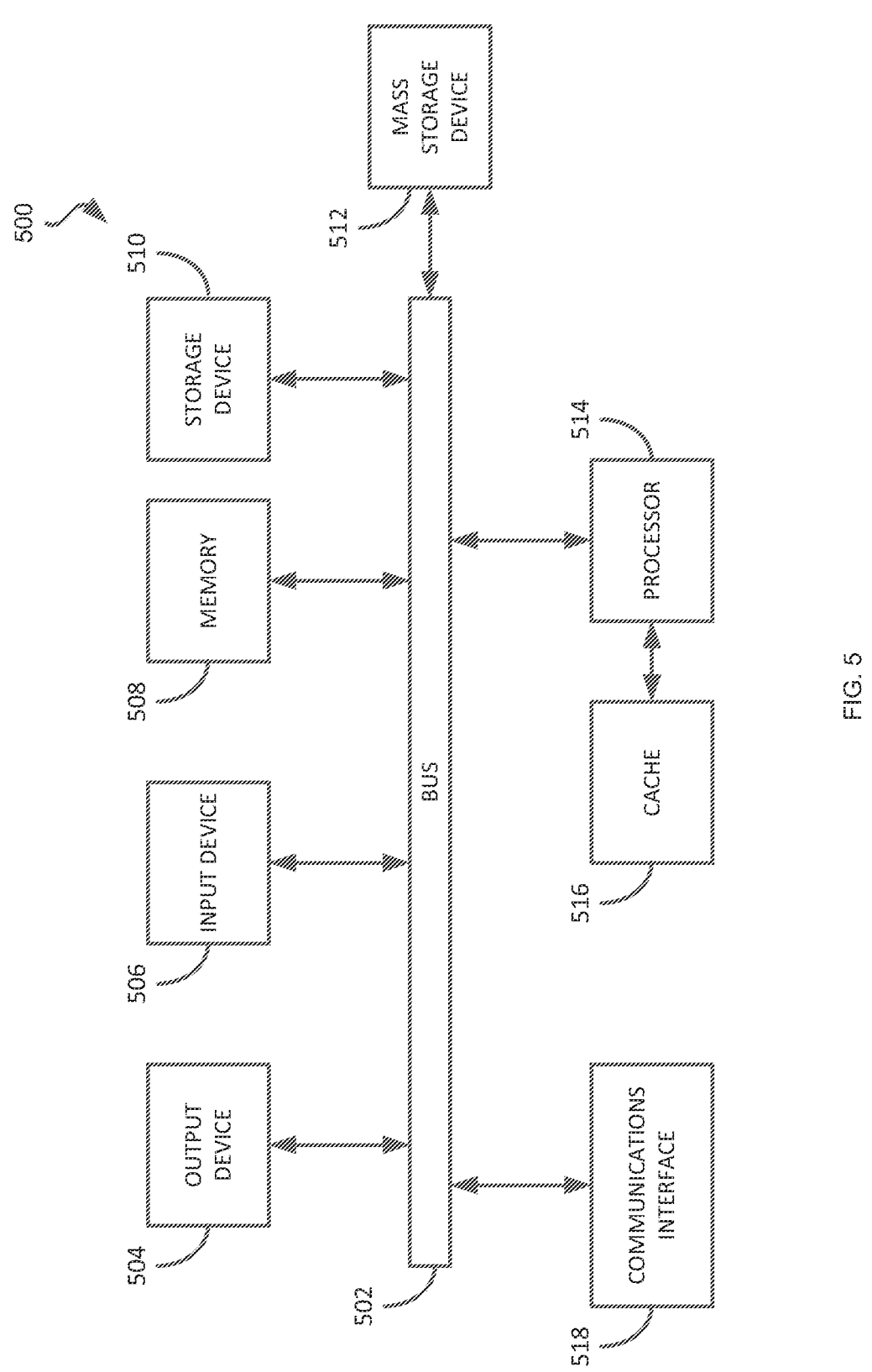
FIG. 5 is a block diagram depicting a system capable of performing the methods of the present disclosure, according one embodiment of the present disclosure.

FIG. 5 depicts an example computing system 500 that may implement various systems and methods discussed herein. The computer system 500 includes one or more computing components in communication via a bus 502. In one implementation, the computing system 500 includes one or more processors 514. The processor 514 can include one or more internal levels of cache 516 and a bus controller or bus interface unit to direct interaction with the bus 502. Memory 508 may include one or more memory cards and a control circuit (not depicted), or other forms of removable memory, and may store various software applications including computer executable instructions, that when run on the processor 514, implement the methods and systems set out herein. Other forms of memory, such as a mass storage device 512, may also be included and accessible, by the processor (or processors) 514 via the bus 502.

The computer system 500 can further include a communications interface 518 by way of which the computer system 500 can connect to networks and receive data useful in executing the methods and system set out herein as well as transmitting information to other devices. The computer system 500 may include an output device 504 by which information can be displayed. The computer system 500 can also include an input device 506 by which information is input. Input device 506 can be a scanner, keyboard, and/or other input devices as will be apparent to a person of ordinary skill in the art. The system set forth in FIG. 5 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the methods can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a computer-readable storage medium having stored thereon instructions, which may be used to program a computer system (or other electronic devices) to perform a process according to the present disclosure. A computer-readable storage medium includes any mechanism for storing information in a form (e.g., software, processing application) readable by a computer. The computer-readable storage medium may include, but is not limited to, optical storage medium (e.g., CD-ROM), magneto-optical storage medium, read only memory (ROM), random access memory (RAM), erasable programmable memory (e.g., EPROM and EEPROM), flash memory, or other types of medium suitable for storing electronic instructions.

The description above includes example systems, methods, techniques, instruction sequences, and/or computer program products that embody techniques of the present disclosure. However, it is understood that the described disclosure may be practiced without these specific details.

While the present disclosure has been described with references to various implementations, it will be understood that these implementations are illustrative and that the scope of the disclosure is not limited to them. Many variations, modifications, additions, and improvements are possible. More generally, implementations in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

We claim:

1. A system for automatically generating, by one or more processors, a structured medical note during a remote medical consultation, the system comprising:

a provider tele-presence device in the vicinity of a medical provider and coupled to a communication network, the provider tele-presence device configured to provide two-way audio communication between the medical provider and a patient in the vicinity of a patient tele-presence device, wherein the provider tele-presence device is configured to display, to the medical provider, information from a medical record of the patient and at least one of the provider tele-presence device and the patient tele-presence device is used to record audio data from communication between the medical provider and the patient;

a machine learning network implemented on the one or more processors receiving the patient's medical record and recorded audio data from the provider tele-presence device, the machine learning network configured to:

distinguish between speech of the medical provider and speech of the patient and remove other voices to obtain patient audio data and medical provider audio data, respectively, electronically transcribe at least the speech of the medical provider from the medical provider audio data, electronically derive patient audio meta-data from the patient audio data, the patient audio meta-data including one or more of slurring in patient speech and a pause duration between a medical provider question and a start of a patient answer; and automatically generate the structured medical note including at least a portion of the medical record, at least a portion of the transcribed speech, and at least a portion of the patient audio meta-data, wherein the structured medical note is stored in the medical documentation server in association with an identity of the patient; and a feedback system implemented on the one or more processors configured to receive medical provider corrections to the automatically generated structured medical note and train the machine learning network based on the medical provider corrections.

2. The system of claim 1, further comprising a patient tele-presence device coupled to the communication network, the patient tele-presence device receiving patient audio from the patient and transmitting the patient audio to the provider tele-presence device, and receiving audio from the provider tele-presence device.

3. The system of claim 2, wherein the machine learning network further receives patient-side data from the patient tele-presence device, the patient-side data including one of visual data or medical device data.

4. The system of claim 2, further comprising a preprocessor, the preprocessor transcribing the patient audio and the medical provider audio data into patient audio text and medical provider audio text, respectively, and providing the patient audio text and the medical provider audio text to the machine learning network.

5. The system of claim 2, wherein the patient tele-presence device comprises one of a desktop computer, mobile device, smartphone, mobile computer, or robotic endpoint.

6. The system of claim 1, wherein the machine learning network executes on one of the patient tele-presence device, the provider tele-presence device, or a server coupled to the communication network.

7. The system of claim 1, wherein the provider tele-presence device further comprises an interface, and wherein the medical provider edits the structured medical note through the interface while it is being generated by the machine learning network.

8. The system of claim 1, wherein the provider tele-presence device further comprises an interface, and wherein the medical provider edits the structured medical note through the interface after it has been generated by the machine learning network.

9. The system of claim 1, wherein the machine learning network further receives provider-side data from the provider tele-presence device, the provider-side data including one of visual data, provider interface interaction data, or clinical documentation data.

10. The system of claim 1, wherein the provider tele-presence device comprises one of a desktop computer, mobile device, smartphone, or mobile computer.

11. The system of claim 1, wherein the provider tele-presence device comprises one of a desktop computer, mobile device, smartphone, or mobile computer.

12. The system of claim 1, wherein the machine learning network receives patient vital sign data from a medical monitoring device connected to the patient and the patient tele-presence device, and wherein the machine learning network automatically generates the structured medical note including at least a portion of the patient vital sign data.

13. The system of claim 1, wherein the patient tele-presence device includes a camera, wherein the patient tele-presence device provides patient video data generated by the camera to the machine learning network, and wherein the machine learning network recognizes patient vital sign data in the patient video data and automatically generates the structured medical note including at least a portion of the patient vital sign data.

14. The system of claim 1, wherein the patient tele-presence device includes a camera, wherein the patient tele-presence device provides patient video data generated by the camera to the machine learning network, and wherein the machine learning network determines a patient posture from the patient video data and automatically generates the structured medical note including at least an indication of the patient posture.

15. The system of claim 1, wherein the machine learning network receives one or more indications of medical provider interactions with the provider tele-presence device including one or more of camera zooms, camera pans, camera tilts, camera switches, or receiving input from a medical peripheral device in the vicinity of the patient, and wherein the machine learning network automatically generates the structured medical note including at least a portion of the one or more indications of the medical provider interactions with the provider tele-presence device.

16. The system of claim 1, wherein the machine learning network uses a medical provider-specific model to generate the structured medical note, and wherein the feedback system is configured to receive the medical provider corrections to the automatically generated structured medical note and train the medical provider-specific model of the machine learning network based on the medical provider corrections.

17. A method for automatically generating, by one or more processors, a structured medical note during a remote medical consultation, the method comprising:

providing, by a provider tele-presence device, two-way audio communication between a medical provider in the vicinity of the provider tele-presence device and a patient in the vicinity of a patient tele-presence device;

displaying, by the provider tele-presence device, information from a medical record of the patient;

recording, by at least one of the provider tele-presence device and the patient tele-presence device, audio data from communication between the medical provider and the patient;

receiving, by a machine learning network implemented on the one or more processors from over a communication network, the patient's medical record and the recorded audio data from the provider tele-presence device distinguishing, by the machine learning network, between speech of the medical provider and speech of the patient and removing other voices to obtain patient audio data and medical provider audio data, respectively;

electronically transcribing, by the machine learning network, at least the speech of the medical provider from the medical provider audio data;

electronically derive patient audio meta-data from the patient audio data, the patient audio meta-data including one or more of slurring in patient speech and a pause duration between a medical provider question and a start of a patient answer;

automatically generating, by the machine learning network, the structured medical note including at least a portion of the medical record, at least a portion of the transcribed speech, and at least a portion of the patient audio meta-data, wherein the structured medical note is stored in a medical documentation server coupled to the communication network in association with an identity of the patient;

receiving, the machine learning network, feedback including medical provider corrections to the automatically generated structured medical note; and training the machine learning network based on the medical provider corrections.

18. The method of claim 17, further comprising receiving, by the machine learning network, the patient audio data from the patient tele-presence device coupled to the communication network, the patient tele-presence device receiving patient audio from the patient and transmitting the patient audio to the provider tele-presence device, and receiving audio from the provider tele-presence device.

19. The method of claim 18, further comprising receiving, by the machine learning network, patient-side data from the patient tele-presence device, the patient-side data including one of visual data or medical device data.

20. The method of claim 18, further comprising transcribing, by a preprocessor, the patient audio data and the medical provider audio data into patient audio text and medical provider audio text, respectively, and providing the patient audio text and the medical provider audio text to the machine learning network.

21. The method of claim 18, wherein the patient tele-presence device comprises one of a desktop computer, mobile device, smartphone, mobile computer, or robotic endpoint.

22. The method of claim 17, further comprising, executing the machine learning network on one of the patient tele-presence device, the provider tele-presence device, or a server coupled to the communication network.

23. The method of claim 17, wherein the provider tele-presence device further comprises an interface, and wherein the method further comprises editing, by the medical provider, the structured medical note through the interface while it is being generated by the machine learning network.

24. The method of claim 17, wherein the provider tele-presence device further comprises an interface, and wherein the method further comprises, editing, by the medical provider, the structured medical note through the interface after it has been generated by the machine learning network.

25. The method of claim 17, further comprising receiving, by the machine learning network, provider-side data from the provider tele-presence device, the provider-side data including one of visual data, provider interface interaction data, and clinical documentation data.

26. The method of claim 17, wherein receiving further comprises receiving patient vital sign data from a medical monitoring device connected to the patient and the patient tele-presence device, and wherein automatically generating comprises automatically generating the structured medical note including at least a portion of the patient vital sign data.

27. The method of claim 17, wherein the patient tele-presence device includes a camera, the method further comprising:
providing, by the patient tele-presence device, patient video data generated by the camera to the machine learning network; and
recognizing, by the machine learning network, patient vital sign data in the patient video data;
wherein automatically generating comprises automatically generating the structured medical note including at least a portion of the patient vital sign data.

28. The method of claim 17, wherein the patient tele-presence device includes a camera, the method further comprising:
providing, by the patient tele-presence device, patient video data generated by the camera to the machine learning network; and
determining, by the machine learning network, a patient posture from the patient video data;
wherein automatically generating comprises automatically generating the structured medical note including at least an indication of the patient posture.

29. The method of claim 17, further comprising:
receiving, from the provider tele-presence device by the machine learning network, one or more indications of medical provider interactions with the provider tele-presence device including one or more of camera zooms, camera pans, camera tilts, camera switches, or receiving input from a medical peripheral device in the vicinity of the patient;
wherein automatically generating comprises automatically generating the structured medical note including at least a portion of the one or more indications of the medical provider interactions with the provider tele-presence device.

30. The method of claim 17, wherein automatically generating comprises using a medical provider-specific model of the machine learning network to automatically generate the structured medical note, and wherein training comprises training the medical provider-specific model of the machine learning network based on the medical provider corrections.

* * * * *